(12) United States Patent
Raghavan et al.

(10) Patent No.: US 6,589,955 B2
(45) Date of Patent: Jul. 8, 2003

(54) PEDIATRIC FORMULATION OF GATIFLOXACIN

(75) Inventors: Krishnaswamy S. Raghavan, Cranbury, NJ (US); Sunanda A. Ranadive, East Brunswick, NJ (US); Kenneth S. Bembenek, Dayton, NJ (US); Loutfy Benkerrour, Paris (FR); Veronique Trognon, La Turballe (FR); Richard G. Corrao, Jackson, NJ (US); Luigi Esposito, Howell, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/143,487

(22) Filed: May 9, 2002

(65) Prior Publication Data

US 2003/0028025 A1 Feb. 6, 2003

(Under 37 CFR 1.47)

Related U.S. Application Data

(60) Provisional application No. 60/299,625, filed on Jun. 20, 2001.

(51) Int. Cl.[7] .................. A61K 31/496; C07D 40/10
(52) U.S. Cl. .................. 514/253.08; 544/363
(58) Field of Search ............. 514/253.08; 544/363

(56) References Cited

U.S. PATENT DOCUMENTS

| 4,865,851 | A | 9/1989 | James et al. |
|---|---|---|---|
| 4,980,470 | A | 12/1990 | Masuzawa et al. |
| 5,043,450 | A | 8/1991 | Masuzawa et al. |
| 5,405,617 | A | 4/1995 | Gowan, Jr. et al. |
| 5,622,978 | A | 4/1997 | Ciceri et al. |
| 5,808,076 | A | 9/1998 | Vetter et al. |
| 5,880,283 | A | 3/1999 | Matsumoto et al. |
| 5,891,469 | A | 4/1999 | Amselem |

FOREIGN PATENT DOCUMENTS

| CA | 2227314 | 1/1998 |
|---|---|---|
| EP | 631787 B1 | 10/1999 |
| RO | 88836 | 3/1986 |
| WO | WO 98/35656 | 8/1998 |
| WO | WO 01/05431 | 1/2001 |

OTHER PUBLICATIONS

C. Baloescu, et al, "Erythromycin Propionate Tablets for Pediatric Use," Chemical Abstracts, vol. 106 (8), p. 377 (col. 1), Feb. 23, 1987, Abstract No. 55949d (RO 88,836–Mar. 31, 1986).

*Primary Examiner*—Emily Bernhardt
(74) *Attorney, Agent, or Firm*—Warren K. Volles

(57) ABSTRACT

There is provided in accordance with the present invention the quinolone antibacterial gatifloxacin adequately taste-masked so that it can be utilized for pediatric formulations. A crystalline co-precipitate of gatifloxacin and one or both of stearic acid and palmitic acid in a narrow weight ratio has been found to effectively mask the bitter taste of gatifloxacin. The taste of gatifloxacin is effectively masked in the mouth and in aqueous suspension through a full dosage cycle, typically fourteen days. Gatifloxacin in the subject crystalline co-precipitates has been found to be readily available for absorption from the stomach.

23 Claims, No Drawings

PEDIATRIC FORMULATION OF GATIFLOXACIN

REFERENCE TO RELATED APPLICATIONS

This application claims the benefit of U.S. Provisional Application Serial No. 60/299,625 filed Jun. 20, 2001.

FIELD OF THE INVENTION

The present invention relates to gatifloxacin suitably taste-masked so that it can be utilized in oral dosage forms, particularly for pediatric formulations.

BACKGROUND OF THE INVENTION

Gatifloxacin, chemically 1-cyclopropyl-6-fluoro-1,4-dihydro-8-methoxy-7-(3-methyl-1-piperazinyl)-4-oxo-3-quinolinecarboxylic acid, is represented by the following structure:

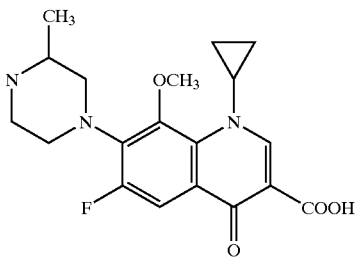

Gatifloxacin is a broad-spectrum quinolone antibacterial that is disclosed and claimed in U.S. Pat. No. 4,980,470. U.S. Pat. No. 5,043,450 discloses gatifloxacin isolated as the hemihydrate. U.S. Pat. No. 5,880,283 discloses a sesquihydrate crystalline form of gatifloxacin that is advantageous over the hemihydrate in pharmaceutical manufacturing. Regardless of the particular form of gatifloxacin, typical of quinolone compounds, it has an extremely bitter taste.

It is recognized that quinolone antibacterials, such as gatifloxacin, have primary application in the treatment of infections in children. Those antibacterials that have a bitter taste are at a considerable disadvantage for pediatric use since many pediatric preparations are in liquid form for ease of administration. Such therapeutic agents can only be administered in liquid dosage forms, including those constituted from dry powder or granules, if the formulations made therefrom have at least an acceptable taste to pediatric patients. Typically, such liquid preparations are available in the form of powders or granules that are mixed with water by a pharmacist at the time of dispensing to form a suspension in a flavored vehicle. The fine particles or granules of active substance in such preparations must either remain suspended in the liquid vehicle or be readily re-dispersed therein simply by shaking the container.

One disadvantage to pediatric suspensions as described above is that, in order to be readily suspended in an aqueous vehicle, the particles/granules of therapeutic agent are very fine. The fineness of the particles exposes a very large surface area to the aqueous vehicle. As a result, leaching of the therapeutic agent can occur, particularly over time. This phenomenon can take place regardless of the mechanism of binding utilized to mask the taste of the therapeutic agent, for example micro-encapsulation. In addition to effectively masking the taste of the therapeutic agent, the binding or coating means employed must maintain the integrity of the granules or particles in the mouth because any appreciable solubilization or leaching of the therapeutic agent by the saliva in the mouth will potentially negate the acceptable flavor of the preparation. Further, although the means of masking the taste of the therapeutic agent must maintain its integrity in the vehicle over a normal course of treatment and in the mouth, it must readily release the therapeutic agent in the stomach for absorption in order for it to be efficacious.

Numerous techniques are known in the art for masking the taste of bitter therapeutic agents. For example, Romanian Patent No. 88836, published Mar. 31, 1986, discloses a process for masking the bitter taste of erythromycin comprising co-precipitation with stearic acid in a ratio of 1:10 utilizing acetone as the common solvent at a temperature not exceeding 40° C. Tablets prepared from the product may be chewed or suspended in a liquid, typically water, for administration. Various other representative techniques focus on the particular taste-masking substance that is mixed with, coated onto or otherwise combined with the bitter-tasting active medicament. Examples of such substances include: acidic phospholipid or lysophospholipid, EP 0 631 787 B1; tocopherol polyethyleneglycol succinate, U.S. Pat. No. 5,891,469; certain ion-exchange resins, WO 01/05431 A1; and embonic acid, a salt or derivative thereof, U.S. Pat. No. 5,808,076. U.S. Pat. No. 5,622,978 discloses amorphous co-precipitates of dihydropyridines and a polymer, such as polyvinyl pyrrolidone, that are administered by dispersing in water. It is stated that the co-precipitates are formed by techniques to minimize crystallinity as crystallinity has a negative effect on bioavailability.

There are also a number of teachings of techniques for coating a bitter-tasting medicament with a waxy substance and then forming a powder therefrom, typically by spray drying, heat-assisted solvent removal and the like. U.S. Pat. No. 5,405,617 discloses a method of taste-masking a bitter pharmaceutical by admixing it with stearyl stearate in the molten state and spray congealing to form a powder. European application EP 0 855 183 A2 discloses a similar process wherein a quinolone derivative and a fatty acid are combined in a blender at a temperature between 30° and 140° C. and blended until a granulation is formed that masks the bitter taste of the drug. In some instances, e.g. Canadian Patent Application 2,227,314, the molten mixture is cooled to solidify it and then granulated. In WO 98/35656, a solution of the bitter-tasting medicament, a lipid and conventional fillers is filled into suitable forms, the solvent is thereafter removed by freeze-drying or other means and the resulting solid mass removed from the molds to yield discrete dosage units. U.S. Pat. No. 4,865,851 discloses taste-masking formulations of cefuroxime axetil by an integral coating of a lipid or mixture of lipids.

Regardless of the numerous techniques and pharmaceutical adjuncts known in the art to mask the taste of bitter-tasting medicaments, there remains the need to find an effective technique, adjunct or combination thereof for specific agents. This has been the case with gatifloxacin, particularly with regard to preparations that would be suitable for pediatric administration. Such preparations are provided in accordance with the present invention. It will be appreciated that, while the usefulness of the taste-masked gatifloxacin formed in accordance with the present invention will be emphasized in regard to pediatric medicine, it is likewise useful for preparations intended for all patients who, as a result of physical challenge or preference, would prefer a liquid preparation. The taste-masked gatifloxacin of the invention is further advantageous in that constituted liquid preparations made therefrom are stable over the normal therapeutic dosage schedule, typically fourteen days.

SUMMARY OF THE INVENTION

In accordance with the present invention, there is provided a form of gatifloxacin having its natural sharply bitter taste sufficiently masked so that it can be effectively utilized in pediatric formulations. Gatifloxacin is formed as a co-precipitate with at least one of stearic acid and palmitic acid in a critical weight ratio. The weight ratio of the two constituents is essential to the advantageous properties of taste-masking and stability of formulations containing it. The present invention further pertains to a process for the preparation of taste-masked gatifloxacin, pharmaceutical formulations containing it and the use thereof in the treatment of a wide variety of infections.

DETAILED DESCRIPTION OF THE INVENTION

In accordance with the present invention, there is provided a taste-masked form of the broad spectrum antibacterial gatifloxacin, 1-cyclopropyl-6-fluoro-1,4-dihydro-8-methoxy-7-(3-methyl-1-piperazinyl)-4-oxo-3-quinolinecarboxylic acid.

Gatifloxacin is approved for use as a broad spectrum antibacterial therapeutic agent. Gatifloxacin has been shown to be both safe and efficacious in the treatment of infections in hepatically impaired individuals. It has also been shown to be effective against a broad spectrum of microorganisms, including antibiotic-resistant strains of *Streptococcus pneumoniae*, and to possess excellent overall tolerability.

In accordance with the present invention, it has been found that the characteristic extremely bitter taste of gatifloxacin can be effectively masked by the formation of a crystalline co-precipitate of gatifloxacin and at least one of stearic acid and palmitic acid in a particular weight ratio. Crystalline forms of gatifloxacin reported in the literature, i.e. the hemihydrate and the sesquihydrate, differ in characteristics and crystalline structure. Although another crystalline form of gatifloxacin could be utilized for the preparation of the subject co-precipitates, the preferred form is the sesquihydrate. The preferred co-precipitant in accordance with the present invention is stearic acid. Crystalline co-precipitates formed in accordance with the present invention have been found to be superior to other recognized mechanisms of combining gatifloxacin with stearic acid, palmitic acid or mixtures thereof in terms of physical characteristics, including stability, and particularly taste-masking. Such other mechanisms include forming a physical mixture, wet or melt granulation and coating of particles of gatifloxacin with the subject fatty acids.

In addition to the fact that the particular mechanism of forming the taste-masked form of gatifloxacin is superior to other methodologies of forming such a composition recognized in the art, it has been found that the use of at least one of stearic acid and palmitic acid to prepare the taste-masked form is advantageous to other art-recognized fatty substances that are often considered at least functionally equivalent thereto by those skilled in the art. Still further, it has been found in accordance with the present invention that a particular narrow weight ratio of gatifloxacin to stearic acid produces optimum parts in comparison to ratios that vary the percentage of the components in favor of one component or the other. While it is known that stearic acid and palmitic acid have been utilized to form taste-masked forms of other therapeutic agents, it is considered unexpected that the form of gatifloxacin formed in accordance with the present invention possesses significant advantages in comparison to similar forms prepared utilizing other fatty substances, by other mechanisms and even wherein the two components are present in different weight ratios.

In accordance with the present invention, there is formed a co-precipitate of gatifloxacin and a fatty acid selected from stearic acid, palmitic acid and mixtures thereof. When the co-precipitate is formed from a mixture of stearic acid and palmitic acid, they are utilized in a weight ratio of from about 1:5 to 5:1, preferably in equal parts by weight. It is preferred to utilize a single fatty acid, most preferably stearic acid, to form the subject co-precipitates. The weight ratio of the fatty acid component to gatifloxacin utilized in forming the co-precipitates of the present invention varies within a rather narrow range for optimum performance. In general, the weight ratio of gatifloxacin to fatty acid in the subject co-precipitates is from about 1:1.8 to 1:2.3, most preferably about 1:2.1. In regard to only the criteria of taste, formulations prepared from co-precipitates of gatifloxacin and stearic acid in weight ratios of 1:0.7, 1:1 and 1:1.4 have a bitter to bland taste, whereas those prepared with weight ratios of 1:2.8 and 1:3 have an increasingly soapy taste. As noted below, however, while taste is an extremely important characteristic of the subject co-precipitates, it is not the only factor to be considered.

The fact that the subject co-precipitates possess unexpectedly superior properties may be explained by the fact that XRD and NMR studies have shown that the co-precipitate formed from gatifloxacin and fatty acid in a weight ratio of 1:2.1 has a different structure than co-precipitates formed therefrom in weight ratios of 1:1.4 and 1:2.8. While the explanation for this is not certain, it might be expected from the observation that, as the weight ratio of gatifloxacin to fatty acid increases from 1:0.7 to 1:2.1, the solubility of the resulting co-precipitate decreases significantly. The solubility of the co-precipitate is important to its capacity to mask the taste of gatifloxacin since any appreciable dissolution in the mouth may produce a bitter taste in spite of the sweetening and flavoring agents present in the formulation. The capacity to mask the bitter taste of gatifloxacin in the mouth is particularly critical for applications in pediatric medicine.

The co-precipitates of the present invention are advantageous in that, as mentioned above, they are virtually unaffected by factors in the mouth, such as pH and enzymes, that would cause them to dissolve, thereby producing a bitter taste. This is clearly critical since gatifloxacin is very bitter. It has been found, however, that the very small amount of gatifloxacin released in the mouth by dissolution of the co-precipitates of the present invention can be effectively masked by conventional flavoring and sweetening agents. It is a significant and unexpected advantage of the crystalline co-precipitates of the present invention that aqueous suspensions formed therefrom which have been stored under normal conditions for a full dosage cycle, typically up to fourteen days, do not undergo dissolution to any material degree. This is a distinct advantage because it is commonly recommended by physicians that their patients take the full cycle of treatment with an antibacterial to prevent the possibility of reoccurrence of infection. If the product were to dissociate upon standing over time to an extent such that the flavoring/sweetening agents present were no longer able to mask the inherent bitterness of a bitter therapeutic agent, such as gatifloxacin, the resultant unpleasant taste might result in the patient not completing the prescribed dosage cycle, particularly if that patient is a child.

As noted earlier, in order to be efficacious, a means of masking the bitter taste of a given therapeutic agent must not only be effective in masking the taste and maintain its integrity both in the mouth and over a typical dosage cycle, it must readily release the therapeutic agent in the stomach for absorption. Dissolution studies using the subject gatifloxacin dry preparation for oral suspension formulation at 40 mg/mL in 0.1N hydrochloric acid, pH 1.2, which simulates stomach conditions, indicate 100% release of gatifloxacin in 10 minutes. Further, comparative clinical oral bioavailability studies using the subject gatifloxacin dry preparation for oral suspension at 40 mg/mL have shown that the bioavailability of gatifloxacin from the suspension is 99% relative to a 400-mg tablet.

The co-precipitates of gatifloxacin and fatty acid of the present invention are prepared by initially dissolving the principal ingredients in a suitable solvent, with heat to effect complete dissolution. Preferred solvents to effect solution are low molecular weight alcohols, most preferably ethanol. Generally, gatifloxacin and the fatty acid component are dispersed into the solvent and the resultant dispersion heated to reflux temperature, generally about 80° C., until all solids have completely dissolved. The amount of solvent added to effect dissolution will typically be sufficient to form a solution containing gatifloxacin in a concentration between about 5% and 10% by weight, preferably between about 6.5% and 8% by weight. While a greater amount of solvent could be utilized to form the solutions, these relatively high concentrations of gatifloxacin are preferred not only for obvious reasons of economy, but to maximize crystal growth as well as ease of handling in subsequent operations as will be described below.

Once solution of the principals of the subject co-precipitates is effected, heating is maintained at reflux temperature, i.e. about 80° C. with mild agitation, i.e. stirring, for an additional 2 to 3 hours, preferably from about 2 to 2.5 hours. The solution is then slowly cooled to about 18° C. with controlled mild agitation to crystallize the co-precipitate. By "slowly cooled" is meant cooling takes place over a period of from about 2.5 to 4 hours. This represents an average cooling rate of from about 0.25° C. to 0.4° C. per minute. As an optional procedure to overcome the inertia typically characteristic of large-scale processing equipment, the solution may be more rapidly cooled to a temperature not below 45° C., and then slowly cooled as described above.

In the cooling step described above, the onset of crystallization is typically characterized by a mild exotherm of several degrees over a period of from about four to eight minutes before cooling resumes. It is important for optimum crystal growth and subsequent handling of the resultant slurry of the desired crystalline co-precipitate that the rate of agitation, i.e. stirring, of the solution be sufficiently mild so that these events, i.e. the onset of crystallization and the mild exotherm, take place at a temperature of from about 32° C. to 35° C. Agitation at an excessive rate will cause both onset of crystallization and mild exotherm to take place as high as 42° C. resulting in a slurry that is very difficult to handle and with poor taste characteristics. The manipulation of the various parameters of amount of solvent utilized, cooling rate and rate of stirring within the constraints given above to accomplish the optimum temperature for onset of crystallization and exotherm is considered to be within the purview of those of ordinary skill in the art.

It will be appreciated from the foregoing discussion that the refluxing and slow cooling steps are important in achieving the desired taste-masking properties of the subject crystalline co-precipitates. The slurry of the subject crystalline co-precipitate formed in the cooling step is maintained at from about 15° to 20° C. with mild stirring for an additional two to eighteen hours, preferably two to four hours, and vacuum filtered to recover the co-precipitate. The wet cake retained on the filter is oven-dried under vacuum at not more than 30 ° C.

In an alternative process, once the solution of the principals of the subject co-precipitates has been formed and heated at reflux as described above, the resultant solution can be directly treated to remove the solvent thereby causing crystallization. This drying treatment may be carried out in an oven, a conventional pan or rotating evaporator, or other similar apparatus. The temperature utilized for solvent removal in an oven is typically between about 400 and 50° C., whereas temperatures in a conventional rotating evaporator may be slightly higher, e.g. from 50° to 60° C. For obvious reasons of economy and the avoidance of solvent disposal issues, the filtration or the drying apparatus is preferably equipped with a means of recovering the solvent to the greatest extent possible so that it may be reused in the process.

The dried co-precipitate is thereafter comminuted to a particle size range that would be suitable to cause the particles to be suspended and periodically redispersed in an aqueous vehicle. In general, an average particle size in the range of 0.5 to 2.0 mm is contemplated, with a particle size range between 0.75 and 1.0 mm being preferred. The comminuting may be carried out on any conventional apparatus equipped with suitable screens to control the size of the resulting particles. It is preferred in accordance with the present invention that the crystalline co-precipitates are initially comminuted to a suitable size as described above and then ground a second time after they have been combined with the excipient materials.

Formulations containing the crystalline co-precipitates of gatifloxacin and a fatty acid are prepared for suspension in an aqueous vehicle by the addition thereto of conventional pharmaceutically acceptable flavoring and sweetening agents. In addition, such formulations may contain pharmaceutically acceptable preservatives, stabilizers, coloring agents, wetting agents and the like. Examples of such agents include: as preservatives, methylparaben, propylparaben and the like; as wetting agents, polyethylene glycol 2000 stearate, sodium lauryl sulfate, polysorbate 80 and the like; as suspending/stabilizing agents, xanthan gum, microcrystalline cellulose, sodium carboxymethylcellulose, hydroxypropyl cellulose and the like; as sweeteners, sodium saccharinate, aspartame, xylitol, sucrose and the like; and as flavoring agents, vanilla, caramel sweet tone, guarana and the like. Such agents are typically utilized in the subject compositions in conventional quantities as recommended by the manufacturer. It is contemplated that such flavoring, sweetening and excipient materials will comprise from about 75 to 90, preferably from about 75 to 85 percent by weight of the final dry formulation.

The formulations containing the subject co-precipitates and the flavoring, sweetening and excipient materials are thoroughly mixed together and, as stated above, preferably again passed through the comminuting device to assure uniform particle size of the final preparation. They are then packaged in appropriate containers. The container may be oversized to accommodate the appropriate amount of water to form a suspension of the co-precipitates and may further be packaged with a second container containing the requisite quantity of purified water. The formulation and packaging of the subject granulations are such that suspensions formed therefrom by the addition of the recommended volume of water would provide a dosage of 200 mg. of gatifloxacin per 5 mL teaspoonful. This dosage may be modified, for example, for forming a suspension that would be dispensed through a dropper calibrated to provide a predetermined amount of gatifloxacin in a given number of drops or portion of a mL.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Preparation of Gatifloxacin-stearic Acid Crystalline Co-precipitate (1:2.1 by Weight)

A 3-necked 500-mL reactor equipped with a mechanical agitator (57 mm Teflon paddle impeller), condenser, heating mantle, and cooling bath was charged with 12.776 g of gatifloxacin sesquihydrate, (31.85 mM, 1 eq,) and 27.225 g of stearic acid (95.71 mM, 3.0 eq,) to which was added 240.0 mL of ethanol, 95% USP. The mixture was heated with agitation to obtain a full reflux (~80° C.) to dissolve the solids. The resultant solution was heated at reflux with stirring for 2.0 hours. The solution was slowly cooled to 18° C. at a cooling-bath rate of 0.25° C. per minute with gentle agitation (80-rpm). Total crystallization required about four hours with solids becoming clearly visible when the solution reached 32.5° C. At the onset of crystallization, the batch temperature rose from 32.5° C. to 35° C. over a period of about five minutes. After this mild exotherm, typical of crystallization procedures, cooling resumed to the desired temperature. The slurry was mixed for a further two hours at 18° C. after which the agitation rate was increased to about 300 rpm for about one minute to maximize batch homogeneity and consistency. The slurry was filtered under vacuum on a 7-cm Buchner funnel fitted with Whatman #4 paper filter media. The reactor was rinsed with only re-circulated mother liquor to discharge the solids therefrom. The wet cake was allowed to drain well by vacuum aspiration and then oven-dried using a 30-in Hg vacuum at 30 ° C. (maximum) until the moisture content by KF attained a value of 1.5% w/w or less. The yield was 37.15 g (36.59 g corrected, 29.78 mM, 93.4 % w/w) of stearic acid-gatifloxacin crystalline co-precipitate with a KF moisture content of 1.5% w/w.

EXAMPLE 2

Formulation of Gatifloxacin Dry Preparation for Oral Suspension

Gatifloxacin dry preparation for oral suspension, 66.1 mg/g.

| Ingredient | Amount per kg |
|---|---|
| Gatifloxacin-Stearic acid Co-precipitate (1:2.1 weight ratio) | 216.7 g[A] |

-continued

| Ingredient | Amount per kg |
|---|---|
| Xylitol | 165.2 g |
| Aspartame | 99.1 g |
| Spray Dried Artificial Guarana Flavor | 1.9 g |
| Flavor, Cream de Vanilla Powder (Natural and Artificial) with 5% Silicon Dioxide | 6.9 g |
| Microcrystalline Cellulose and Sodium Carboxymethylcellulose (Avicel RC-591) | 2.8 g |
| Methylparaben | 2.3 g |
| Propylparaben | 0.3 g |
| Titanium Dioxide | 5.4 g |
| Sucrose | 499.4 g |

[A]216.7 g of Gatifloxacin-Stearic acid Co-precipitate is equivalent to 66.1 g of Gatifloxacin, based on 100% purity.

All ingredients were combined and blended for about 10 minutes at about 25 RPM to form a preblend that was then passed through a Fitzmill equipped with a 0.61 mm screen. The milled material was transferred back to the blender and mixed again for about 10 minutes at about 25 RPM. Calculated amounts of the final blend were filled into appropriately sized high-density polypropylene (HDPE) bottles. For example, 63.7 g of the dry preparation was filled into a 200-mL HDPE bottle, which when constituted with 46 mL of water results in 105 mL of suspension containing 40 mg of gatifloxacin per mL. The suspensions were taste-tested over a period of 14 days, which represents a typical dosage cycle for an antibacterial preparation. The results showed that the taste characteristics of the suspensions remained unchanged and satisfactory, indicating that the suspensions were stable over the storage period.

What is claimed is:

1. A crystalline co-precipitate of gatifloxacin and a fatty acid selected from the group consisting of stearic acid, palmitic acid and mixtures thereof, wherein the weight ratio of gatifloxacin to said fatty acid is from about 1:1.8 to 1:2.3.

2. A crystalline precipitate in accordance with claim 1, wherein the weight ratio of gatifloxacin to said fatty acid is about 1:2.1.

3. A crystalline co-precipitate in accordance with claim 1, wherein said fatty acid is stearic acid.

4. A crystalline co-precipitate in accordance with claim 2, wherein said fatty acid is stearic acid.

5. A crystalline co-precipitate in accordance with claim 1, wherein said fatty acid is palmitic acid.

6. A crystalline co-precipitate in accordance with claim 2, wherein said fatty acid is palmitic acid.

7. A crystalline co-precipitate in accordance with claim 1, wherein said fatty acid is a mixture of stearic acid and palmitic acid in a weight ratio of from about 1:5 to 5:1.

8. A crystalline co-precipitate in accordance with claim 7, wherein said fatty acid is a mixture of stearic acid and palmitic acid in about equal parts by weight.

9. A pharmaceutical composition intended for suspension in water for oral administration comprising a crystalline co-precipitate in accordance with claim 1 and pharmaceutically acceptable excipients.

10. A pharmaceutical composition in accordance with claim 9, wherein said pharmaceutically acceptable excipients comprise at least one member selected from the group consisting of water-soluble flavoring agents and sweeteners.

11. A pharmaceutical composition in accordance with claim 9, wherein the fatty acid in the crystalline co-precipitate is stearic acid.

12. A pharmaceutical composition in accordance with claim 9, wherein the fatty acid in the crystalline co-precipitate is palmitic acid.

13. A pharmaceutical composition in accordance with claim 9, wherein the fatty acid in the crystalline co-precipitate is a mixture of stearic acid and palmitic acid in a weight ratio of from about 1:5 to 5:1.

14. A method for treating infections in a mammal in need thereof comprising orally administering to the mammal an effective amount of an aqueous suspension of the pharmaceutical composition of claim 9.

15. A method for treating infections in a mammal in need thereof comprising orally administering to the mammal an effective amount of an aqueous suspension of the pharmaceutical composition of claim 10.

16. A method for treating infections in a mammal in need thereof comprising orally administering to the mammal an effective amount of an aqueous suspension of the pharmaceutical composition of claim 11.

17. A method in accordance with claim 14, wherein said aqueous suspension contains a sufficient amount of said crystalline precipitate to provide a dosage of 200 mg. of gatifloxacin in each 5 mL thereof.

18. A process of forming a crystalline co-precipitate of gatifloxacin and a fatty acid selected from the group consisting of stearic acid, palmitic acid and mixtures thereof comprising:

a) dissolving gatifloxacin and said fatty acid in a weight ratio of from about 1:1.8 to 1:2.3 in a suitable solvent with heating to reflux temperature to effect solution thereof;

b) refluxing said solution for from two to three hours with stirring;

c) slowly cooling said solution with stirring to about 18° C. over a period of from about 2.5 to 4 hours to precipitate the crystalline co-precipitate of gatifloxacin and said fatty acid;

d) maintaining the resultant slurry of said crystalline co-precipitate to about 15° C. to 20° C. for an additional two to four hours; and e) recovering and drying said crystalline co-precipitate.

19. A process in accordance with claim 18, wherein said solution is formed in step a) with gatifloxacin sesquihydrate.

20. A process in accordance with claim 18, wherein said fatty acid is stearic acid.

21. A crystalline co-precipitate formed by the process of claim 18.

22. A crystalline co-precipitate formed by the process of claim 19.

23. A crystalline co-precipitate formed by the process of claim 20.

* * * * *